United States Patent [19]

Falch et al.

[11] Patent Number: 4,608,378

[45] Date of Patent: Aug. 26, 1986

[54] TETRAHYDROISOXAZOLO[4,5-c]PYRIDINE DERIVATIVES USEFUL IN THE TREATMENT OF MALFUNCTIONS OF THE ACETYLCHOLINE OR MUSCARINIC SYSTEMS

[75] Inventors: Erik Falch, Vedbaek; Povl Krogsgaard-Larsen, Allerod; Per Sauerberg, Copenhagen-Valby; Anne V. Christensen, Farum; Jens-Jorgen Larsen, Hillerod, all of Denmark

[73] Assignee: H. Lundbeck A/S, Copenhagen-Valby, Denmark

[21] Appl. No.: 611,697

[22] Filed: May 18, 1984

[30] Foreign Application Priority Data

May 24, 1983 [GB] United Kingdom ............... 8314391

[51] Int. Cl.[4] ................ A61K 31/44; C07D 498/04
[52] U.S. Cl. ................................ 514/302; 546/116
[58] Field of Search ............... 546/116; 424/256; 514/302

[56] References Cited

PUBLICATIONS

Krogsgaard et al., J. Labelled Compounds Radio Pharm., vol. 19(5), pp. 689–702, (1982).

*Primary Examiner*—Richard A. Schwartz
*Assistant Examiner*—Bernard I. Dentz
*Attorney, Agent, or Firm*—Gordon W. Hueschen

[57] ABSTRACT

The present invention relates to novel compounds of the following formula:

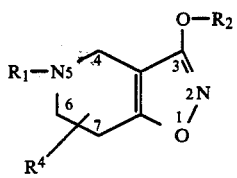

individual isomers and pharmaceutically acceptable acid addition salts thereof, wherein $R_1$ is hydrogen, alkyl or phenyl-lower alkyl, in which the phenyl group may be substituted with halogen, lower alkyl or lower alkoxy; $R_2$ is alkyl, alkenyl, alkynyl or phenyl-lower alkyl, in which the phenyl group may be substituted with halogen, lower alkyl or lower alkoxy; and $R_4$ is hydrogen or alkyl.

The invention moreover relates to methods for the preparation of the compounds of formula I, to novel intermediates, to pharmaceutical compositions containing same and to methods for the treatment of disorders, caused by malfunction of the acetylcholine (AcCh) or muscarinic system, by administering a non-toxic effective amount of a compound of the formula I.

16 Claims, No Drawings

TETRAHYDROISOXAZOLO[4,5-C]PYRIDINE DERIVATIVES USEFUL IN THE TREATMENT OF MALFUNCTIONS OF THE ACETYLCHOLINE OR MUSCARINIC SYSTEMS

BACKGROUND OF THE INVENTION

AcCh is known to be a neurotransmitter in the peripheral as well as the central nervous system (CNS). Reduced function of AcCh in the CNS, probably as a result of degeneration of neurones utilizing AcCh as a neurotransmitter, is believed to be related to the etiology of various diseases such as Alzheimers disease and Down's syndrome (R. M. Marchbanks, *J. Neurochem.* 39 (1982) 9-15; R. D. Terry and P. Davies, *Ann. Rev. Neurosci.*, 3 (1980) 77; N. R. Sims, D. M. Bowen, S. J. Allen, C. C. T. Smith, D. Neary, D. J. Thomas and A. N. Davidson, *J. Neurochem.*, 40 (1983) 503-509; E. Roberts, in *Ann. New York Acad. Sci.* (F. Marott Sinex and C. R. Merril, editors), 396 (1982) 165-178. Furthermore, senile dementia, which may be associated with aging, appears to be somehow related to decreased AcCh activity in the CNS, and similarly impaired learning and memory functions have been associated with decreased functions of the central AcCh-system (P. S. Anderson and D. Haubrich, *Ann.Rep.Med.Chem.*, 16 (1981) 51-60. Administration of agents capable of stimulating the central AcCh-system is therefore under consideration and research for the therapeutical treatment of such AcCh-system malfunction-related diseases. Compounds capable of activating the AcCh receptors, AcCh agonists, are assumed to be of primary interest. However, most known AcCh agonists, including AcCh itself, contain quaternary ammonium groups and, consequently, these compounds do not penetrate the blood-brain barrier (BBB) easily after peripheral administration. As a result of this, such compounds do not reach the AcCh receptors in the CNS but activate almost exclusively the peripheral AcCh receptors, which are unrelated to the diseases mentioned above, provoking various undesired effects.

Arecoline (methyl 1-methyl-1,2,5,6-tetrahydropyridine-3-carboxylate) is an AcCh agonist, which does not contain a quaternary ammonium group. Arecoline is a tertiary amine, and arecoline is capable of penetrating the BBB after peripheral administration. The ester group of arecoline is, however, very rapidly hydrolyzed in vivo, and arecoline has very weak and frequently negligible central effects after peripheral administration.

DETAILED DESCRIPTION OF THE INVENTION

According to the present invention, it has now surprisingly been found that the novel compounds of Formula I have very potent AcCh agonist activity. In the design of these compounds great importance has been attached to the following factors:

(1) The 3-alkoxyisoxazole units are isosteric with ester groups containing the same alkoxy groups. In contrast to ester groups the respective 3-alkoxyisoxazole units are not susceptible to hydrolysis under physiological conditions.

(2) The $pK_a$ values are comparable with physiological pH values (pH 7.1-7.4). This means that considerable fractions of peripherally administered doses of the compounds will exist in the unionized form in the blood stream and, consequently, the compounds in all probability penetrate the BBB very rapidly.

Moreover, the compounds of Formula I have very low toxicity as compared to therapeutic effective doses.

This invention also includes pharmaceutically acceptable salts of the compounds of Formula I formed with non-toxic organic or inorganic acids. Such salts are easily prepared by methods known to the art.—The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly.—Exemplary of such organic salts are those with maleic, fumaric, benzoic, ascorbic, embonic, succinic, oxalic, bis methylene-salicylic, methanesulfonic, ethanedisulfonic, acetic, propionic, tartaric, salicylic, citric, glucomic, lactic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromo-theophylline.—Exemplary of such inorganic salts are those with hydrochloric, hydrobromic, sulfuric, sulfamic, phosphoric and nitric acids. Of course, these salts may also be prepared by the classical method of double decomposition of appropriate salts, which is well-known to the art.

When $R_4$ is different from hydrogen the compounds of formula I can be separated into two enantiomeric forms. Likewise, when $R_2$ contains a double bond the compounds of formula I may exist in an E- and a Z-form. It is understood, that the present invention encompasses all enantiomers and mixtures thereof, as well as both the E- and the Z-forms and mixtures thereof.

In the present context, the term "alkyl" designates $C_{1-6}$ alkyl which may be straight or branched, such as methyl, ethyl, propyl, isopropyl, butyl, tert.butyl, pentyl or hexyl. Among the alkyl groups, lower alkyl groups are preferred. The term "lower alkyl" designates $C_{1-4}$ alkyl which may be straight or branched, such as methyl, ethyl, propyl, isopropyl, butyl, or tert.butyl. The term "alkenyl" designates a $C_3$-$C_6$ straight or branched alkyl group which contains a double bond, such as 2-propenyl, 2-butenyl, 2-pentenyl, 2-hexenyl, 2-methyl-2-propenyl or 3-methyl-2-butenyl. The term "alkynyl" designates a $C_3$-$C_6$ straight or branched alkyl group containing a triple bond, such as 2-propynyl, 2-butynyl, 2-pentynyl, 2-hexynyl or 4-methyl-2-pentynyl. The term "phenyl-lower-alkyl" designates a lower alkyl group (as herin defined) which, in turn, is substituted with a phenyl group. Preferred phenyl-lower-alkyl are benzyl, 1- and 2-phenylethyl, 1-, 2- and 3-phenylpropyl, and 1-methyl-1-phenylethyl.—Where the phenyl group is substituted with halogen, lower alkyl, or lower alkoxy, they may be mono-, or di-, or tri-substituted, and when they are di- or tri-substituted the substituents may be the same or different. The term "lower alkoxy" designates oxy to which is attached a lower alkyl group. Preferred groups are methoxy and ethoxy. The term "halogen" designates F, Cl, Br, or I; Cl and Br are preferred.

Specific examples of preferred compounds of the Formula I are:

3-Methoxy-4,5,6,7-tetrahydroisoxazolo[4,5-c]pyridine (O-Methyl-THPO)

3-Ethoxy-4,5,6,7-tetrahydroisoxazolo[4,5-c]pyridine (O-Ethyl-THPO)

3-Propoxy-4,5,6,7-tetrahydroisoxazolo[4,5-c]pyridine (O-Propyl-THPO)
3-Isopropoxy-4,5,6,7-tetrahydroisoxazolo[4,5-c]pyridine (O-Isopropyl-THPO)
3-Benzyloxy-4,5,6,7-tetrahydroisoxazolo[4,5-c]pyridine (O-Benzyl-THPO)
3-Methoxy-5-methyl-4,5,6,7-tetrahydroixoxazolo[4,5-c]pyridine (O,5-Dimethyl-THPO)
3-Ethoxy-5-methyl-4,5,6,7-tetrahydroisoxazolo[4,5-c]pyridine (O-Ethyl-5-methyl-THPO)
3-Propoxy-5-methyl-4,5,6,7-tetrahydroisoxazolo[4,5-c]pyridine
3-Isopropoxy-5-methyl-4,5,6,7-tetrahydroisoxazolo[4,5-c]pyridine
3-Benzyloxy-5-methyl-4,5,6,7-tetrahydroisoxazolo[4,5-c]pyridine
3-(4-Chlorobenzyloxy)-4,5,6,7-tetrahydroisoxazolo[4,5-c]pyridine
3-(4-Methylbenzyloxy)-4,5,6,7-tetrahydroisoxazolo[4,5-c]pyridine
3-(4-Methoxybenzyloxy)-4,5,6,7-tetrahydroisoxazolo[4,5-c]pyridine
3-(4-Chlorobenzyloxy)-5-methyl-4,5,6,7-tetrahydroisoxazolo[4,5-c]pyridine
3-(4-Methylbenzyloxy)-5-methyl-4,5,6,7-tetrahydroisoxazolo[4,5-c]pyridine
3-(4-Methoxybenzyloxy)-5-methyl-4,5,6,7-tetrahydroisoxazolo[4,5-c]pyridine
3-Methoxy-5-ethyl-4,5,6,7-tetrahydroisoxazolo[4,5-c]pyridine (O-Methyl-5-ethyl-THPO)
3-Ethoxy-5-ethyl-4,5,6,7-tetrahydroisoxazolo[4,5-c]pyridine
3-Propoxy-5-ethyl-4,5,6,7-tetrahydroisoxazolo[4,5-c]pyridine
3-Isopropoxy-5-ethyl-4,5,6,7-tetrahydroisoxazolo[4,5-c]pyridine
3-Benzyloxy-5-ethyl-4,5,6,7-tetrahydroisoxazolo[4,5-c]pyridine
3-Methoxy-5-propyl-4,5,6,7-tetrahydroisoxazolo[4,5-c]pyridine
3-Ethoxy-5-propyl-4,5,6,7-tetrahydroisoxazolo[4,5-c]pyridine
3-Benzyloxy-5-propyl-4,5,6,7-tetrahydroisoxazolo[4,5-c]pyridine
3-Methoxy-5-isopropyl-4,5,6,7-tetrahydroisoxazolo[4,5-c]pyridine
3-Ethoxy-5-isopropyl-4,5,6,7-tetrahydroisoxazolo[4,5-c]pyridine
3-Methoxy-5-butyl-4,5,6,7-tetrahydroisoxazolo[4,5-c]pyridine
3-Ethoxy-5-butyl-4,5,6,7-tetrahydroisoxazolo[4,5-c]pyridine
3-Methoxy-5-benzyl-4,5,6,7-tetrahydroisoxazolo[4,5-c]pyridine (O-Methyl-5-benzyl-THPO)
3-Ethoxy-5-benzyl-4,5,6,7-tetrahydroisoxazolo[4,5-c]pyridine
3-Methoxy-5-(4-chlorobenzyl)-4,5,6,7-tetrahydroisoxazolo[4,5-c]pyridine
3-Methoxy-5-(4-methylbenzyl)-4,5,6,7-tetrahydroisoxazolo[4,5-c]pyridine
3-Methoxy-5-(4-methoxybenzyl)-4,5,6,7-tetrahydroisoxazolo[4,5-c]pyridine
3-Butoxy-4,5,6,7-tetrahydroisoxazolo[4,5-c]pyridine (O-Butyl-THPO)
3-Isobutoxy-4,5,6,7-tetrahydroisoxazolo[4,5-c]pyridine (O-Isobutyl-THPO)
3-Allyloxy-4,5,6,7-tetrahydroisoxazolo[4,5-c]pyridine (O-Allyl-THPO)
3-(2-Butenyloxy)-4,5,6,7-tetrahydroisoxazolo[4,5-c]pyridine (O-Crotyl-THPO)
3-(2-Propynyloxy)-4,5,6,7-tetrahydroisoxazolo[4,5-c](O-Propargyl-THPO)
3-Allyloxy-5-methyl-4,5,6,7-tetrahydroisoxazolo[4,5-c]pyridine
3-(2-Butenyloxy)-5-methyl-4,5,6,7-tetrahydroisoxazolo[4,5-c]pyridine
3-(2-Propynyloxy)-5-methyl-4,5,6,7-tetrahydroisoxazolo[4,5-c]pyridine
3-Methoxy-4-methyl-4,5,6,7-tetrahydroisoxazolo[4,5-c]pyridine
3-Methoxy-6-methyl-4,5,6,7-tetrahydroisoxazolo[4,5-c]pyridine
3-Methoxy-7-methyl-4,5,6,7-tetrahydroisoxazolo[4,5-c]pyridine (O,7-dimethyl-THPO)
3-Isopropoxy-7-methyl-4,5,6,7-tetrahydroisoxazolo[4,5-c]pyridine
3-Allyloxy-7-methyl-4,5,6,7-tetrahydroisoxazolo[4,5-c]pyridine
3-(2-Propynyloxy)-7-methyl-4,5,6,7-tetrahydroisoxazolo[4,5-c]pyridine
3-Methoxy-5,7-dimethyl-4,5,6,7-tetrahydroisoxazolo[4,5-c]pyridine
and salts thereof.

Especially preferred compounds are:
3-Methoxy-4,5,6,7-tetrahydroisoxazolo[4,5-c]pyridine
3-Ethoxy-4,5,6,7-tetrahydroisoxazolo[4,5-c]pyridine
3-Methoxy-5-methyl-4,5,6,7-tetrahydroisoxazolo[4,5-c]pyridine
3-Ethoxy-5-methyl-4,5,6,7-tetrahydroisoxazolo[4,5-c]pyridine
3-Methoxy-7-methyl-4,5,6,7-tetrahydroisoxazolo[4,5-c]pyridine
3-Allyloxy-4,5,6,7-tetrahydroisoxazolo[4,5-c]pyridine
3-(2-Butenyloxy)-4,5,6,7-tetrahydroisoxazolo[4,5-c]pyridine
3-(2-Propynyloxy)-4,5,6,7-tetrahydroisoxazolo[4,5-c]pyridine
and salts thereof.

The compounds of Formula I may—according to the invention—be prepared by (a) reacting a compound of the Formula II

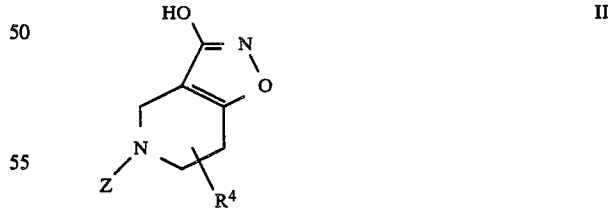

in which $R_4$ is as defined above and Z is an amino-protecting group readily removable, e.g. by hydrolysis or hydrogenation with a compound of the Formula III

R$_2$—X            III in which $R_2$ is as defined above, and X is a leaving group, and removing the group Z by hydrolysis or hydrogenation, or (b) reacting a compound of the Formula IV

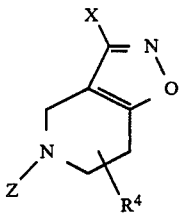

in which $R_4$, X and Z are as defined above, with an alcohol of the Formula V $$R_2\text{—OH} \qquad \qquad V$$

in which $R_2$ is as defined above, or (c) reacting a compound of the Formula I, in which $R_1$ is hydrogen and $R_2$ and $R_4$ are as defined above, with an aldehyde of the Formula VI

   VI in which $R_3$ is hydrogen, alkyl or phenyl, which may be substituted with halogen, lower alkyl or lower alkoxy; or phenyl-lower-alkyl in which the phenyl group may be substituted with halogen, lower alkyl or lower alkoxy in the presence of a reducing agent, or (d) reacting a compound of the Formula I, in which $R_1$ is hydrogen and $R_2$ and $R_4$ are as defined above, with a compound of the general formula VII

   VII in which $R_3$ and X are as defined above, and reducing the resulting compound of the following formula:

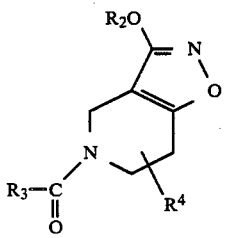   VIII with a reducing agent (e.g. lithium aluminhydride, diborane, cyanoborohydride or the like), or (e) reacting a compound of the formula IX

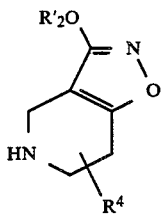   IX in which $R'_2$ is hydrogen or a group $R_2$ as defined above, and $R_4$ is as defined, with a compound of formula III, in which $R_2$ and X are as defined, whereupon the compound of Formula I formed is isolated as the free base or a non-toxic pharmaceutically acceptable acid addition salt thereof and, if desired, the individual isomers isolated.

Specific examples of Z in formulas II and IV are the following: Methoxycarbonyl, ethoxycarbonyl, propoxycarbonyl, tert.butoxycarbonyl, benzyloxycarbonyl, 4-chlorobenzyloxycarbonyl, trityl, formyl or acetyl.

As examples of leaving groups X may be mentioned chlorine, bromine, iodide.

In method (a) the reaction is preferably performed in a solvent, e.g. acetone, a lower alcohol, toluene or N,N-dimethylformamide in the presence of a base, e.g. potassium carbonate, a metal hydride, a tertiary amine, or a metal alcoholate. The reaction is carried out at a temperature from 0° C. to the boiling point of the solvent, and for a period of time from 1–96 hours. The removal of the group Z may be performed in wellknown manner, e.g. by hydrolysis or hydrogenation, and then, if desired, a group $R_1$ may be introduced by one of the methods (c) or (d).

In method (b) the reaction is normally performed in a solution of excess of the alcohol of formula V, which may contain from 0% to 50% water, and in the presence of a base, e.g. a metal hydroxide or a metal alcoholate. The reaction temperature will usually be in the range of 0°–150° C., preferably from 0° C. to the boiling point of the alcohol of the formula V. In many cases, especially when the reaction mixture contains water, the amino-protecting group Z is removed by hydrolysis during the reaction. Otherwise, the group Z may be removed in wellknown manner, e.g. by hydrolysis or hydrogenation, and then, if desired, a group $R_1$ may be introduced by one of the methods (c) or (d).

In method (c) the reaction is performed in the presence of a reducing agent, e.g. formic acid, diborane or cyanoborohydride in a solvent, e.g. an ether, methanol, chloroform or dioxane, at a temperature from −20° C. to 100° C.

In method (d) the intermediate of formula VIII is mostly not isolated but may be so, if desired. Otherwise, the compound of formula VIII formed in the reaction mixture may without isolation be treated with a reducing agent, e.g. lithium aluminhydride, diborane or cyanoborohydride. The reaction may be performed in an inert solvent, e.g. an ether, toluene or dioxane, at a temperature from −20° C. to the boiling point of the solvent.

In method (e) the reaction is preferably performed in a solvent, e.g. acetone, a lower alcohol, toluene or N,N-dimethylformamide, in the presence of a base, e.g. potassium carbonate, a metal hydroxide, a tertiary amine or a metal alcoholate. The reaction is carried out at a temperature from 0° C. to the boiling point of the solvent and for a period of time from 0 to 96 hours.

The invention also relates to further novel intermediates for preparing the compound of the formula I.

The novel intermediates are of the formula X

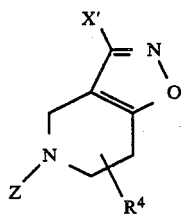   X in which Z and $R_4$ are as defined above and X' is chlorine, bromine or iodine.

The compounds of the formula X may be prepared by reacting a compound of the formula XI

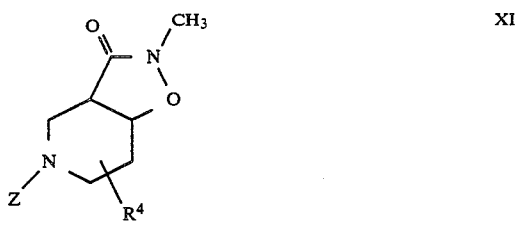

with a halogenating agent, e.g. phosphorus oxychloride, phosphorus pentachloride, phosphorus oxybromide or a mixture of iodine and phosphorous. The reaction is normally performed by using excess of the halogenating agent as a solvent but may also be carried out in an inert solvent, e.g. chloroform or toluene. The reaction temperatures are preferably between room temperature and the boiling point of either the halogenating agent or, if a solvent is used, the boiling point of the solvent.

The preparation of various intermediates and compounds of formula I will appear from the following page with reaction schemes.

The reaction from compound 6 to compounds 7 and 8 may be carried out, as shown, with diazomethane, and this reaction is described in the litterature for the preparation of deuterium-labelled compounds of the structure shown. The use of diazomethane as a methylating agent is, however, extremely hazardous in view of the toxic and explosive nature of this agent and only applicable in small laboratory scale.

The preparation of the intermediates and compounds of formula I will be illustrated in the following by examples which may not be construed as limiting. The numbers are referring to the numbers in the reaction scheme, and the following litterature references:

1. S. Morosawa, *Bull.Chem.Soc.Japan* 31 (1958) 418-422.
2. P. Krogsgaard-Larsen and H. Hjeds, *Acta Chem.-Scand.B* 28 (1974) 533-538.
3. P. Krogsgaard-Larsen, J. S. Johansen and E. Falch, *J. Labelled Compd.* 19 (1982) 689-702.

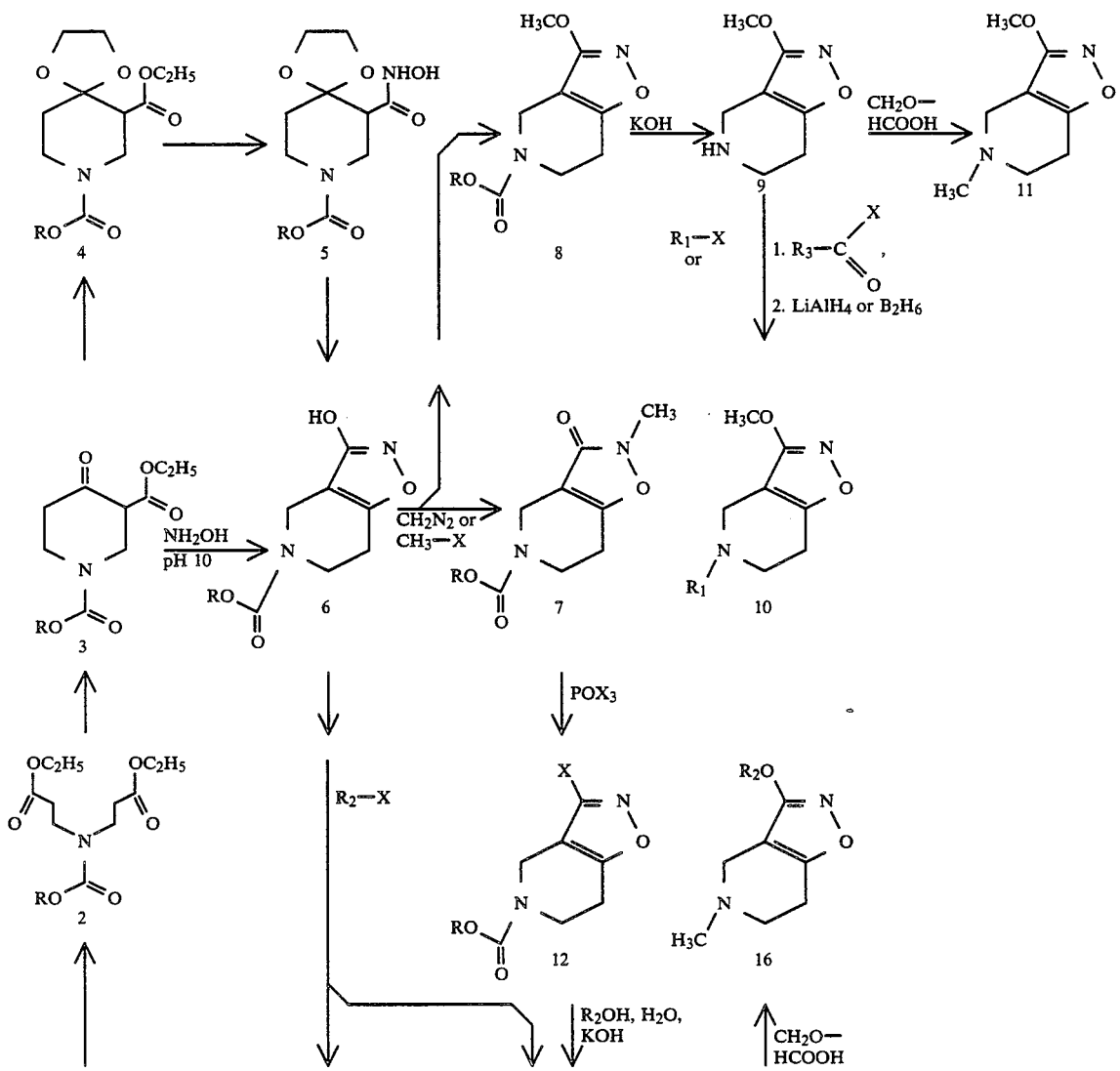

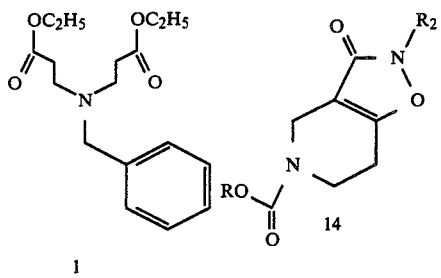
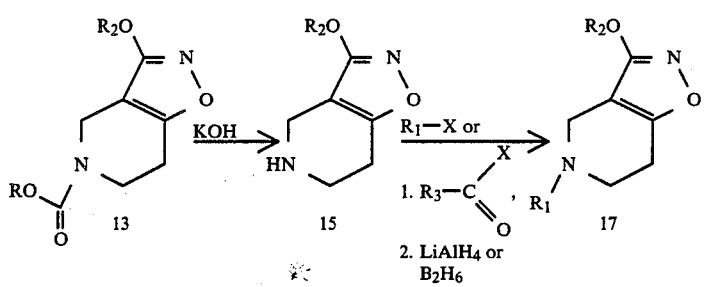

EXAMPLE 1

Ethyl N-methoxycarbonyl-3-(2-ethoxycarbonylethylamino)-propionate(2; R=Me)

A solution of $1^1$ (160 g; 0.52 mol) and methyl chloroformate (172 g; 1.8 mol) in 1,2-dichloroethane (500 ml) was refluxed for 7 hours. Distillation of the evaporated reaction mixture afforded 2 (R=Me) (140 g; 98%), b.p. 162°–164° C./4 mm Hg. Anal. ($C_{12}H_{21}O_6N$) C, H, N.

EXAMPLE 2

Ethyl N-ethoxycarbonyl-3-(2-ethoxycarbonylethylamino)-propionate (2; R=Et)

This compound was synthesized as described for 2 (R=Me) using $1^1$ (30.7 g; 0.1 mol), ethyl chloroformate (54.3 g; 0.5 mol) and 1,2-dichloroethane (100 ml). Obtained 2 (R=Et) (25.6 g; 89%), b.p. 170°–180° C./2.5–3 mm Hg. Anal. ($C_{13}H_{23}O_6N$) C, H, N.

EXAMPLE 3

Ethyl 1-methoxycarbonyl-4-oxopiperidine-3-carboxylate (3; R=Me)

To a suspension of sodium ethoxide, prepared from sodium (2.2 g; 0.094 mol) and ethanol (17.4 g; 0.38 mol), in toluene (50 ml) was added dropwise and while stirring 2 (R=Me) (26 g; 0.094 mol) at 25° C. The mixture was heated at 120° C. for 45 min., and upon standing at 25° C. for 16 h the precipitate was isolated by filtration and washed with ethyl acetate. To a solution of this salt in water (100 ml) was added dichloromethane (100 ml), and with stirring at 0° C. hydrochloric acid (25 ml; 4M) was added. The two phases were separated, the aqueous phase extracted twice with dichloromethane (100 ml) and the combined organic phases dried (MgSO4) and evaporated in vacuo to give TLC-pure crude 3 (R=Me) (15.4 g) [eluent: toluene-ethyl acetate-acetic acid (49:49:2); $R_F$:0.43.] B.p. 141°–142° C./0.9 mm Hg.

EXAMPLE 4

Ethyl 1-ethoxycarbonyl-4-oxopiperidine-3-carboxylate (3; R=Et)

Compound 3 (R=Et) was synthesized as described for 3 (R=Me) using 2 (R=Et) (27.2 g; 0.094 mol). Obtained was TLC-pure crude 3 (R=Et) (15.9 1 g) [eluent: toluene-ethyl acetate-acetic acid (49:49:2); $R_F$:0.46] B.p. 130°–138° C./0.6 mm Hg.

EXAMPLE 5

Ethyl 1-methoxycarbonyl-4-oxopiperidine-3-carboxylate ethylene ketal (4; R=Me) and ethyl 1-ethoxycarbonyl-4-oxopiperidine-3-carboxylate ethylene ketal (4; R=Et)

These compounds were prepared in analogy with an earlier described procedure[2] using toluene instead of benzene as an azeotropic solvent.

4(R=Me) B.p. 160°–162° C./0.4 mm Hg.
4(R=Et) B.p. 152°–156° C./0.2 mm Hg.

EXAMPLE 6

1-Methoxycarbonyl-4-oxopiperidine-3-carbohydroxamic acid ethylene ketal (5; R=Me)

To a solution of hydroxylamine hydrochloride (15.1 g; 0.22 mol) in methanol (110 ml) was added during a period of 2 min. at 40° C. a solution of sodium methoxide, prepared from sodium (5.0 g; 0.22 mol) and methanol (55 ml). Upon cooling of the mixture to 17° C. a solution of 4 (R=Me) (39.7 g; 0.15 mol) in methanol (20 ml) and subsequently during a period of 5 min. a solution of sodium methoxide, prepared from sodium (5.0 g; 0.22 mol) and methanol (55 ml), was added and the mixture left at 25° C. for 3 d. A solution of hydrogen chloride in ethanol-ethyl acetate, prepared from ethanol (60 ml) and acetyl chloride (18.5 g; 0.23 mol), was added with stirring. During this addition the temperature was kept below 20° C. The filtered reaction mixture was evaporated and the oily residue dissolved in ethyl acetate (150 ml). The mixture was filtered and left at 5° C. for 4 d., after which 5 (R=Me) (27.9 g; 74%) was isolated as crystals.—M.p. 162°–165° C.

EXAMPLE 7

1-Ethoxycarbonyl-4-oxopiperidine-3-carbohydroxamic acid ethylene ketal (5; R=Et)

Compound 5 (R=Et) was synthesized as described for 5 (R=Me) using 4 (R=Et) (43.1 g; 0.15 mol).

5 (R=Et) (30.1 g; 73%) M.p. 134.5°–136.5° C.

EXAMPLE 8

Methyl 3-hydroxy-4,5,6,7-tetrahydroisoxazolo[4,5-c]pyridine-5-carboxylate (6; R=Me)

Compound 6 (R=Me) was synthesized in analogy with an earlier described procedure[2]. M.p. 155.0°–156.5° C.

EXAMPLE 9

Ethyl 3-hydroxy-4,5,6,7-tetrahydroisoxazolo[4,5-c]pyridine-5-carboxylate (6; R=Et)

Compound 6 (R=Et) was synthesized in analogy with an earlier described procedure[2].—M.p. 118.0°–120.5° C.

EXAMPLE 10

Methyl 3-methoxy-4,5,6,7-tetrahydroisoxazolo[4,5-c]pyridine-5-carboxylate (8; R=Me) and methyl 2-methyl-3-oxo-2,3,4,5,6,7-hexahydroisoxazolo[4,5-c]pyridine-5-carboxylate (7; R=Me)

The compounds 8 (R=Me) and 7 (R=Me) were synthesized and separated chromatographically as described earlier[3] using 6 (R=Me) (10.2 g; 0.051 mol). Obtained were 8 (R=Me) (5.70 g; 52%), M.p. 55°–57° C., and 7 (R=Me) (4.60 g; 42%), M.p. 64°–64° C. (ethyl acetate-light petroleum). Anal. ($C_9H_{12}O_4N_2$) C, H, N.

EXAMPLE 11

Ethyl 3-methoxy-4,5,6,7-tetrahydroisoxazolo[4,5-c]pyridine-5-carboxylate (8; R=Et) and ethyl 2-methyl-3-oxo-2,3,4,5,6,7-hexahydroisoxazolo[4,5-c]pyridine-5-carboxylate (7; R=Et)

To a suspension of 6 (R=Et) (8.23 g; 0.039 mol) in ether (50 ml) was added with stirring an ether solution of diazomethane (ca. 2.50 g; 0.060 mol) prepared from N-methyl-N-nitroso-4-toluenesulphonamide (17.2 g; 0.080 mol). After stirring for 2 hours the remaining diazomethane was destroyed (formic acid). TLC [eluent: toluene-ethyl acetate (1:1)] revealed the presence of two components in the evaporated reaction mixture ($R_F$ 0.44 and 0.04). The two components, 8 (R=Et) and 7 (R=Et) respectively, were separated by column chromatography (CC) [eluent: toluene-ethyl acetate (3:2)] to give 8 (R=Et) (5.60 g; 64%), M.P. 48°–50° C. (toluene-light petroleum). Anal. ($C_{10}H_{14}O_3N_2$) C, H, N., and 7 (R=Et) (3.00 g; 34%), MP 96°–97° C. Anal. ($C_{10}H_{14}O_4N_2$), C, H, N.

EXAMPLE 12

3-Methoxy-4,5,6,7-tetrahydroisoxazolo[4,5-c]pyridinium chloride (9,HCl)=(15,HCl; $R_2$=Me)

Method 1

This compound was synthesized from 8 (R=Me) as described earlier[3]. The hydrochloride of 9 was also synthesized from 8 (R=Et) in analogy with the procedure based on 8 (R=Me)[3] using 8 (R=Et) (5.80 g; 0.026 mol) and methanolic potassium hydroxide (54 ml; 4M). After reflux for 3 hours the reaction mixture was worked up to give 9,HCl (3.75 g; 77%).—MP 191° C. (decomp.).

Method 2

The compound was also synthesized directly from 12 (R=Et, X=Cl). A solution of 12 (R=Et, X=Cl) in a solution of potassium hydroxide (300 mg; 0.005 mol) in water (0.15 ml) and methanol (4 ml) was refluxed for 3 hours. Upon addition of glacial acetic acid (0.025 ml) the reaction mixture was evaporated in vacuo. Upon addition of an aqueous solution of potassium hydroxide (5 ml; 2M) the mixture was extracted with chloroform (3×50 ml). To the combined, dried (MgSO$_4$), and filtered chloroform phases was added a solution of hydrogen chloride in ethyl acetate (5 ml; 1.3M). The crystals of 15,HCl ($R_2$=Me) 15 mg; 26%) were isolated and melted at 191° C. with decomp.

EXAMPLE 13

Ethyl 3-chloro-4,5,6,7-tetrahydroisoxazolo[4,5-c]pyridine-5-carboxylate (12; R=Et, X=Cl)

A solution of 7 (R=Et) (678 mg; 0.003 mol) in phosphorus oxychloride (6 ml) was heate at 100° C. for 48 hours. The dark solution was evaporated. Upon addition of water (50 ml) the mixture was extracted with ethyl acetate (2×75 ml). The combined organic phases were washed with a saturated solution of sodium hydrogen carbonate (30 ml), dried (MgSO$_4$), and evaporated to give an oil. CC eluent: toluene-ethyl acetate (5:1) gave 12 (R=Et, X=Cl) (276 mg; 40%), M.P. 40°–42° C. (toluene-light petroleum). Anal. ($C_9H_{11}O_3N_2Cl$), C, H, N, Cl.

EXAMPLE 14

3-Methoxy-5-ethyl-4,5,6,7-tetrahydroisoxazolo[4,5-c]pyridinium chloride (10,HCl; $R_1$=Et)

Compound 9,HCl (381 mg; 0.002 mol) was heated with a solution of potassium carbonate (553 mg; 0.004 mol) in water (5 ml) and the mixture was extracted with chloroform (3×15 ml). The combined and dried ($K_2CO_3$) chloroform phases were evaporated in vacuo and the residue dissolved in dry pyridine (1.5 ml). Upon addition of acetic anhydride (0.75 ml) the solution was heated at 100° C. for 15 min. Upon evaporation in vacuo water (15 ml) was added to the oily residue and the mixture extracted with chloroform (3×15 ml). The combined, dried (MgSO$_4$), and filtered chloroform phases were evaporated to give TLC-pure (eluent: ethyl acetate) crude 3-methoxy-5-acetyl-4,5,6,7-tetrahydroisoxazolo[4,5-c]pyridine (433 mg), of which an analytical sample was crystallized (light petroleum) to give pure compound, M.P. 40°–42° C. Anal. ($C_9H_{12}O_3N_2$) C, H, N. To a solution of crude 3-methoxy-5-acetyl-4,5,6,7-tetrahydroisoxazolo[4,5-c]pyridine (392 mg; ca. 0.002 mol) in dry ether (6 ml) was added lithium aluminium hydride (304 mg; 0.003 mol). The mixture was refluxed for 1 h, after which wáter (2 ml) and then an aqueous solution of sodium hydroxide (1 ml; 33%) were added. The ether phase was isolated, dried (MgSO$_4$), and filtered, and upon addition of a solution of hydrogen chloride in ethyl acetate (5 ml; 1.3M), 10,HCl ($R_1$=Et) (105 mg; 24%), based on 9,HCl), M.P. 180° C. (decomp.) Anal. ($C_9H_{15}N_2Cl$) C, H, N, Cl.

EXAMPLE 15

Methyl 3-methoxy-4,5,6,7-tetrahydroisoxazolo[4,5-c]pyridine-5-carboxylate (8; R=Me)

To a solution of 6 (R=Me) (9.92 g; 50 mmol) in acetone (400 ml) was added potassium carbonate (17.3 g; 125 mmole) and the mixture was stirred at 50° C. for 1 h. At this temperature methyl iodide (9.4 ml; 150 mmol) was added dropwise and the mixture was stirred for 20 h. The reaction mixture was filtered and the filtrate evaporated in vacuo. To the residue was added water (30 ml), and the mixture was extracted with chloroform (3×4 ml). The combined extracts were dried and evaporated in vacuo. The resulting yellow oil contained both the O-methyl- and the N-methyl-alkylated starting compound. The two compounds were separated by CC using silica gel and toluene-ethyl acetate mixtures as an eluent. The first fractions containing 8 (R=Me) (2.44 g; 23%) were collected. M.P. 58°-60° C.

EXAMPLE 16
Methyl 3-ethoxy-4,5,6,7-tetrahydroisoxazolo[4,5-c]pyridine-5-carboxylate (13; R=Me; $R_2$=Et)

To a solution of 6 (R=Me) (9.92 g; 50 mmol) in acetone (600 ml) was added potassium carbonate (17.3 g; 125 mmol), and the mixture was stirred at 50° C. for 1 h. At this temperature, a solution of ethyl bromide (11,3 ml; 150 mmol) in acetone (15 ml) was added dropwise, ahd the mixture was stirred for 20 hours. The reaction mixture was filtered and the filtrate evaporated in vacuo. To the residue was added water (40 ml) and the mixture was stirred for 1 h at room temperature yielding 13 (R=Me; $R_2$=Et) as a white crystalline solid (7.01 g; 62%). Recrystallization from cyclohexane gave an analytically pure product, M.P. 95°-98° C.

EXAMPLE 17
Methyl 3-propoxy-4,5,6,7-tetrahydroisoxazole[4,5-c]pyridine-5-carboxylate (13; R=Me; $R_2$=Propyl)

13 (R=Me; $R_2$=Propyl) was synthesized as described above in Example 16 using propyl bromide instead of ethyl bromide. The yield of crude product was 56%. Recrystallization from ligroin yielded an analytically pure product, M.P. 48°-52° C.

EXAMPLE 18
Methyl 3-benzyloxy-4,5,6,7-tetrahydroisoxazolo[4,5-c]pyridine-5-carboxylate (13; R=Me; $R_2$=Benzyl)

13 (R=Me; $R_2$=Benzyl) was synthesized as described above in Example 15 using benzyl bromide instead of methyl iodide. The crude 13 (R=Me; $R_2$=Benzyl) was isolated as an oil in a yield of 24%. $^1$H NMR (CDCl$_3$): 7.45 (5H, s), 5.25 (2H, s), 4.35 (2H, m), 3.75 (3H, s), 3.75 (2H, perturbed t), 2.75 (2H, m).

EXAMPLE 19
3-Ethoxy-4,5,6,7-tetrahydroisoxazolo[4,5-c]pyridinium chloride (15; $R_2$=Et)

A solution of 13 (R=Me; $R_2$=Et) (1.7 g; 7.5 mmol) and potassium hydroxide (4.0 g; 76 mmol) in methanol (20 ml) and water (4 ml) was refluxed for 1 hour. The mixture was evaporated in vacuo. Under addition of water (10 ml) the residue was extracted with chloroform (3×30 ml). After drying, the chloroform was evaporated and excess of 2N hyrochloric acid was added. The mixture was evaporated in vacuo, and the residue recrystallized from acetonitrile, yielding analytically pure 15 ($R_1$=H; $R_2$=Et) (966 mg; 62%), M.P. 190°-193° C.

EXAMPLE 20
3-Propoxy-4,5,6,7-tetrahydroisoxazolo[4,5-c]pyridinium chloride (15; $R_2$=Propyl)

15 ($R_1$=H; $R_2$=Propyl) was synthesized as described above in Example 19 using 13 (R=Me; $R_2$=Propyl) as starting material. The yield of analytically pure 15 ($R_1$=H; $R_2$=Propyl) was 59%, M.P. 184°-186° C.

EXAMPLE 21
3-Benzyloxy-4,5,6,7-tetrahydroisoxazolo[4,5-c]pyridinium chloride (15; $R_2$=Benzyl)

15 ($R_1$=H; $R_2$=Benzyl) was synthesized as described above in Example 19 using 13 (R=Me; $R_2$=Benzyl) as starting material. The yield of analytically pure 15 ($R_1$=H; $R_2$=Benzyl) was 49%, M.P. 190°-193° C.

EXAMPLE 22
3-Methoxy-5-methyl-4,5,6,7-tetrahydroisoxazolo[4,5-c]pyridinium chloride (11) (17;$R_1$=Me; $R_2$=Me)

9,HCl (1.33 g; 7 mmol) was added to a solution of potassium carbonate (1,38 g; 10 mmol) in water (15 ml) and the mixture was extracted with chloroform (3×15 ml). The extracts were dried and evaporated. Formic acid (7 ml) and a 35% aqueous solution of formaldehyde (7 ml) were added to the residue, and the mixture was stirred at 100° C. for 1 h. The reaction mixture was evaporated in vacuo. A solution of potassium carbonate (1.38 g; 10 mmol) in water (15 ml) was added to the residue, and the mixture was extracted with chloroform (3×15 ml). The chloroform was dried and evaporated, and a solution of hydrochloric acid in ethyl acetate (10 ml; 13 mmol) was added to the residue. The crude product (1.31 g; 91%) was collected and recrystallized from methanol, yielding analytically pure 11 ($R_1$=Me; $R_2$=Me) (1.05 g; 73%), M.P. 210° C.

EXAMPLE 23
3-Ethoxy-5-methyl-4,5,6,7-tetrahydroisoxazolo[4,5-c]pyridinium chloride (17; $R_1$=Me; $R_2$=Et)

17 ($R_1$=Me; $R_2$=Et) was synthesized as described above in Example 22, using 15 ($R_1$=H; $R_2$=Et) as starting material. The crude product was recrystallized from 2-propanol yielding analytically pure 17 ($R_1$=Me; $R_2$=Et) (88%), M.P. 180°-184° C.

EXAMPLE 24
Methyl 3-isopropoxy-4,5,6,7-tetrahydroisoxazolo[4,5-c]pyridine-5-carboxylate (13; R=Me, $R_2$=iso-propyl)

The compound was synthesized as described above in Example 15 using excess isopropyl bromide instead of methyl iodide. The crude 13 (R=Me, $R_2$=isopropyl) was isolated as an oil. $^1$H NMR (CDCl$_3$): 4.95 (1H, m), 4.30 (2H,m), 3.75 H NMR (CDCl$_3$) (3H,s), 3.75 (2H, pertubed t), 1.35 (6H,d).

EXAMPLE 25
3-Isopropoxy-4,5,6,7-tetrahydroisoxazolo[4,5-c]pyridinium chloride (15; $R_2$=Isopropyl)

15 ($R_1$=H, $R_2$=Isopropyl) was synthesized as described above in Example 19 using 13 (R=Me, $R_2$=Isopropyl) as starting material. The yield of analytically pure 15 ($R_1$=H, $R_2$=Isopropyl) was 57%; M.P. 185°-188° C.

EXAMPLE 26

Methyl 3-allyloxy-4,5,6,7-tetrahydroisoxazolo[4,5-c]pyridine-5-carboxylate (13; R=Me; R$_2$=Allyl)

13 (R=Me; R$_2$=Allyl) was synthesized as described above in Example 15 using allyl bromide instead of methyl iodide. The crude product (M.P. 39°–41° C.) was isolated in a yield of 40%. $^1$H NMR (CDCl$_3$): 5.8–6.4 (1H, m), 5.2–5.6 (2H,m), 4.75 (2H,d), 4.3 (2H,s), 5.7 (5H,t), 2.7 (2H,t).

EXAMPLE 27

3-Allyloxy-4,5,6,7-tetrahydroisoxazolo[4,5-c]pyridinium chloride (15; R$_2$=Allyl)

15 (R$_2$=Allyl) was synthesized as described above in Example 19 using 13 (R=Me; R$_2$=Allyl) as starting material. The yield of analytically pure 15 (R$_2$=Allyl) was 75%, M.P. 144°–145° C.

EXAMPLE 28

Methyl 3-butoxy-4,5,6,7-tetrahydroisoxazolo[4,5-c]pyridine-5-carboxylate (13; R=Me; R$_2$=Butyl)

13 (R=Me; R$_2$=Butyl) was synthesized as described above in Example 15 using butyl bromide instead of methyl iodide. Instead of CC the O- and the N-butylalkylated starting compounds were separated by extraction with light petroleum from a mixture of water and the two compounds. Recrystallization of the crude extracts from light petroleum yielded an analytically pure title compound in 62% yield, M.P. 41°–42° C.

EXAMPLE 29

3-Butoxy-4,5,6,7-tetrahydroisoxazolo[4,5-c]pyridinum chloride (15; R$_2$=Butyl)

15 (R$_2$=Butyl) was synthesized as described above in Example 19 using 13 (R=Me; R$_2$=Butyl) as starting material. The reaction mixture was refluxed for 15 hours and the yield of the crude product was 92%. Recrystallization from acetonitrile yielded an analytically pure product, M.P. 178°–180° C.

EXAMPLE 30

Methyl 3-isobutoxy-4,5,6,7-tetrahydroisoxazolo[4,5-c]pyridine-5-carboxylate (13; R=Me; R$_2$=Isobutyl)

To a solution of sodium methoxide (5 mmol) in methanol was added 6 (R=Me) (1.0 g; 5 mmol). The solution was evaporated in vacuo and N,N-dimethylacetamide (15 ml), potassium iodide (50 mg), and isobutyl bromide (1.7 ml; 15 mmol) were added to the residue. The mixture was stirred at 80° C. for 20 h and evaporated in vacuo. Water (10 ml) was added to the residue and the mixture was extracted three times with 20 ml portions of chloroform/2-propanol (3:1). The combined extracts were washed with water, dried, and evaporated. The resulting yellow oil contained both the O-isobutyl and N-isobutyl-alkylated starting compound. Water (20 ml) was added to the oil and the mixture was extracted twice with light petroleum (100 ml). The combined extracts were washed with water, dried, and evaporated yielding 0.49 g (38%) of crude 13 (R=Me; R$_2$=Isobutyl). $^1$H NMR: 4.35 (2H,s), 4.1 (2H,d), 3.8 (5H,t), 2.7 (2H,t), 2.05 (1H,m), 1.0 (6H,d).

EXAMPLE 31

3-Isobutyl-4,5,6,7-tetrahydroisoxazolo 4,5-c pyridinium chloride (15; R$_2$=Isobutyl)

15 (R$_2$=Isobutyl) was synthesized as described above in Example 19 using 13 (R=Me; R$_2$=Isobutyl) as starting material and refluxing the reacting mixture for 15 hours. The yield of analytically pure title compound was 63%, M.P. 195°–196° C.

EXAMPLE 32

(E)-Methyl 3-(2-butenyloxy)-4,5,6,7-tetrahydroisoxazolo[4,5-c]pyridine-5-carboxylate(13; R=Me; R$_2$=2-Butenyl)

13 (R=Me; R$_2$=2-Butenyl) was synthesized as described above in Example 28 using crotyl bromide instead of butyl bromide. The yield of the crude product was 41%. Recrystallization from light petroleum gave an analytically pure compound, M.P. 68°–69° C.

EXAMPLE 33

(E)-3-(2-Butenyloxy)-4,5,6,7-tetrahydroisoxazolo[4,5-c]pyridinium chloride (15; R$_2$=2-Butenyl)

15 (R$_2$=2-Butenyl) was synthesized as descibed above in Example 19 using 13 (R=Me; R$_2$=2-Butenyl) as starting material. Recrystallization from methanolethyl acetate-ether gave the analytically pure title compound in a yield of 35%, M.P. 156°–157° C.

EXAMPLE 34

3-Methoxy-5-benzyl-4,5,6,7-tetrahydroisoxazolo[4,5-c]pyridinium chloride (17; R$_1$=Benzyl; R$_2$=Me)

A suspension of 9,HCl (1.5 g; 7.9 mmol) and potassium carbonate (2.8 g; 20 mmol) in acetone (70 ml) was stirred at 50° C. for 1 h. Benzyl chloride (2.05 ml; 17.8 mmol) was added dropwise and the mixture was stirred for 20 hours at 50° C. The mixture was filtered and the filtrate was evaporated in vacuo. Water (15 ml) was added to the residue and the mixture was extracted with three 70 ml-portions of ethyl acetate. The combined and dried extracts were concentrated to 20 ml, and an excess of hydrochloric acid in ethyl acetate was added separating crude 17 (R$_1$=Benzyl; R$_2$=Me). Recrystallization from methanol-ether gave an analytically pure product in a yield of 65%, M.P. 202°–204° C.

EXAMPLE 35

3-Hydroxy-4,5,6,7-tetrahydroisoxazolo[4,5-c]pyridinium bromide (15; R$_2$=H)

To a 33% solution of hydrobromic acid in acetic acid (75 ml) was added 10 g (50 mol) of 6 (R=Me) and the solution was left in the dark for 8 days. Evaporation of the reaction mixture in vacuo and recrystallization of the residue from methanol yielded 82% of analytically pure title compound M.P. 158°–160° C.

EXAMPLE 36 tert.Butyl 3-hydroxy-4,5,6,7-tetrahydroisoxazolo[4,5-c]pyridine-5-carboxylate (6; R=tert.Butyl)

To a mixture of 3.00 g (13.5 mmol) of 15 (R$_2$=H) hydrobromide and potassium carbonate (1.86 g; 13.5 mmol) was added a solution of pyrocarbonic acid ditert-.butyl ester (5.2 ml; 22.5 mmol) and the mixture was stirred at room temperature for 20 hours. The reaction mixture was evaporated in vacuo and the residue dissolved in water (25 ml). The aqueous solution was washed twice with ethyl acetate (25 ml), cooled in an ice bath and covered with ethyl acetate (150 ml). The mixture was carefully acidified with hydrochloric acid to pH=3 and the phases were separated. The aqueous phase was further extracted with ethyl acetate (50 ml) and the combined ethyl acetate phases were dried and evaporated. Recrystallization of the residue from toluene-light petroleum gave the analytically pure title compound in a yield of 57%, M.P. 151°–152° C.

EXAMPLE 37 tert.Butyl 3-(2-propynyloxy)-4,5,6,7-tetrahydroisoxazolo[4,5-c]pyridine-5-carboxylate (13;R=tert.Butyl; $R_2$=2-Propynyl)

A mixture of 1.5 g (6.25 mmol) of 6 (R=tert.Butyl) and potassium carbonate (1.8 g; 13 mmol) in acetone (75 ml) was stirred at 50° C. for 1 hour, and propargylbromide (1.45 ml; 19 mmol) was added. The reaction mixture was refluxed for 20 hours, filtered, and the filtrate was evaporated in vacuo. The residue was three times extracted with 50 ml of light petroleum containing 5% chloroform. The combined extracts were washed with water, dried and evaporated. Recrystallization of the residue from ether gave an analytically pure product in a yield of 30%, M.P. 107°–108° C.

EXAMPLE 38

3-(2-Propynyloxy)-4,5,6,7-tetrahydroisoxazolo[4,5-c]pyridinium chloride (15; $R_2$=2-Propynyl)

To a solution of 0.45 g (1.6 mmol) of 13 (R=tert.Butyl; $R_2$=2-Propynyl) in ethyl acetate (20 ml) was added an excess of 2N hydrochloric acid in ethyl acetate. After stirring for 24 hours at room temperature the precipitate was collected and recrystallized from acetonitrile-ether. The yield of analytically pure title compound was 74%, M.P. 176°–177° C.

EXAMPLE 39

(RS)-Ethyl 1-methoxycarbonyl-4-oxo-5-methylpiperidine-3-carboxylate ethylene ketal A mixture of 1.9 g (7.8 mmol) of (RS)-ethyl 1-methoxycarbonyl-4-hydroxy-5-methyl-1,2,5,6-tetrahydropyridine-3-carboxylate (prepared as described in Acta Chem. Scand. B32, 327 (1978)), ethylene glycol (2.2 ml), 4-toluenesulfonic acid (0.15 g), and toluene was refluxed for 20 hours using a Dean-Stark water separator. The mixture was washed with aqueous sodium bicarbonate, dried and evaporated in vacuo. The crude product was distilled at 0.5 mm Hg, B.P. 148°–152° C. Yield 1.6 g.

EXAMPLE 40

(RS)-1-Methoxycarbonyl-4-oxo-5-methylpiperidine-3-carbohydroxamic acid ethylene ketal The compound was prepared from (RS)-ethyl 1-methoxycarbonyl-4-oxo-5-methylpiperidine-3-carboxylate ethylene ketal in analogy with the procedure described above in Example 6. The crude product was an oil.

EXAMPLE 41

(RS)-Methyl 3-hydroxy-7-methyl-4,5,6,7-tetrahydroisoxazolo[4,5-c]-pyridine-5-carboxylate (RS)-1-Methoxycarbonyl-4-oxo-5-methylpiperidine-3-carbohydroxamic acid ethylene ketal (3.95 g; 14.4 mmol) was at 5° C. added in small portions to a mixture of 96% $H_2SO_4$ (9 ml) and water (1 ml). The mixture was then kept at 50° C. for 30 min. and poured on ice. The pH was adjusted to 3 with 9N sodium hydroxide and the mixture was extracted three times with methylene chloride (75 ml). Evaporation in vacuo yielded 2.23 g of crude product. To obtain an analytically pure sample the crude product was purified by CC (eluent: ethyl acetate containing 2% methanol and 2% glacial acetic acid). Recrystallization from toluene yielded the pure title compound, M.P. 128°–129° C.

EXAMPLE 42

(RS)-Methyl 3-methoxy-7-methyl-4,5,6,7-tetrahydroisoxazolo[4,5-c]pyridine-5-carboxylate The compound was prepared from (RS)-methyl 3-hydroxy-7-methyl-4,5,6,7-tetrahydroisoxazolo[4,5-c]pyridine-5-carboxylate in analogy with the procedure described in Example 11 above. The analytically pure compound was an oil. $^1$H NMR (CDCl$_3$): 4.25 (2H,d), 3.95 (3H,s), 3.70 (3H,s), 3.1–2.7 (3H,m), 1.25 (3H,d).

EXAMPLE 43

(RS)-3-Methoxy-7-methyl-4,5,6,7-tetrahydroisoxazolo[4,5-c]pyridinium chloride

The compound was synthesized from (RS)-methyl 3-methoxy-7-methyl-4,5,6,7-tetrahydroisoxazolo[4,5-c]pyridine-5-carboxylate in analogy with the procedure described in Example 19. Recrystallization from methanol-ether yielded an analytically pure product, M.P. 196°–197° C.

The novel compounds of Formula I, as well as their acid addition salts, were tested according to reliable standard pharmacological tests, which may be described as follows:

In the screening programme a fixed dose schedule is used, as follows: 320, 160, 80, 40, 20, 10, 5, 2.5, 1.25, 0.63, 0.31, 0.16, 0.08, 0.04, 0.02, 0.01, 0.005, 0.0025, 0.0012 and 0.00063 mg/kg. A schedule showing the corresponding dosages in micromoles/kg is also indicated ED 50 values are given in micromoles/kg.

The concentration range for in vitro tests depends on the kind of investigation. The range used will appear from the record.

"i.v. LD50" is the figure in the fixed dose range that is closest to LD50. This dose is the highest dose used in the screening. When LD50 has been determined i.p. the highest dose in the screening is ¼ "i.p. LD50", defined in the same way as "i.v. LD50". The numbers connected with each test are the numbers under which they have been recorded on the computer.

The ED50 values of the computer out-put have been calculated by means of probit analysis (logarithmic dose scale), and the SD-FACTOR is calculated in such a way that the interval (ED50÷SD-FACTOR)−(ED50×SD-FACTOR) indicates the approximate 95% confidence interval for the true ED50 value.

"Minimal effective dose" is the lowest dose showing significant effect compared to the control group.

Certain tests may be run on line on the terminal. The on line process provides punching instruction and punching cards.

Animals

If nothing else is indicated, the following species are used:
Mice, ♂, NMRI/BOM, SPF
Rats, ♂, Mol/Wist., SPF
Guinea pigs, ♂ or ♀

Hot Plate Test

A group of 10 rats was used for each dose. Each rat was placed on a 55° C. hot plate and the reaction time in seconds was recorded from the moment the rat was placed on the plate until the rat reacted to the heat stimulus. The criteria for reaction were licking of paws, lifting of legs or jumping. The rat was removed from the plate immediately after the reaction. The rat was rejected if the reaction time was more than 10 seconds. After control testing the test substance was injected subcutaneously. The rat was tested on the hot plate 30 minutes after the injection and the reaction times were recorded. A cut-off time of 30 seconds was used. The results were expressed as mean percent effect (MPE), and ED50 values were calculated.

Mouse Grid Shock

Mice, male, 20–23 g.

The mouse grid consists of a perspex cage with wire grid bottom and a perspex lid, on which is placed a microphone sensitive to the frequency of mouse-squeak. A stimulator with motordriven potentiometer applies a sequence of square wave impulses of continuously increasing milliamperage to the grid. Frequence of impulses 20 cycles/sec., duration 5 msec. Milliamperage is recorded on a digital amperemter connected to the stimulator. Activation of the microphone by a mouse-squeak cuts off the current and the final milliamperage appear on the meter.

Dosage and procedure

The test substance is given i.p. in the doses ½, ¼ and ⅛ of the determined "i.v. LD50". For insoluble substances the doses ¼, ⅛ and 1/16 of the "i.p. LD50" are used. Five mice are used for each dose level. Each mouse serves as its own control. Prior to the administration of test substance the animals are placed on the grid one at a time, and the pain threshold is determined by increasing the current intensity until the mouse squeaks. The pain threshold may be read on the milliampermeter. Fifteen minutes and 30 minutes after administration of test substance the mice are tested again and the pain thresholds recorded. Furthermore, the test substance may be tested after oral administration in the doses 1/1, ½ and ¼ of "the i.v. LD50", and the pain threshold is determined before and 30 minutes after the administration. Insoluble test substances are tested orally in the doses of ½, ¼ and ⅛ of the "i.p. LD50".

Analgesic effect is present when the pain threshold is increased over the predosing value (control value). The results are stated as % increase in pain threshold calculated on the basis of the control value. The registration can also be done as an on-line procedure. In this case the punching instruction and punching cards will be provided automatically, and the results will be registered as a minimal effective dose (MED) determined after van der Waerden's X-test.

Isoniazide antagonism

Mice, male, 20–25 g.
Isoniazide 300 mg/kg s.c.
Macrolon cages type II

Dosage and procedure

The test compound is injected i.p. in the doses 0, ½, ⅛ and 1/32 of the determined "i.v. LD50". In case of insoluble substances the doses 0, ¼, 1/16 and 1/64 of the determined "i.p. LD50" are used. Five mice are used for each dose level. Immediately after administration of test substance, isoniazide 300 mg/kg is injected s.c. This dose of isoniazide induces intermittent tonic clonic seizures within 60 minutes.

The calculations are performed as an "on-line procedure" on the EDP-terminal. The results are recorded as % increase in time until convulsions occur and, $ED_{50}$ values were determined.

Muscarinic cholinergic agonism, guinea pig ileum

Guinea pigs 400–600 g.
Tyrode solution (NaCl 137 mM, KCl 2.7 mM, $CaCl_2$ 1.8 mM, $MgCl_2$ 1.1 mM, $NaH_2PO_4$ 0.32 mM, $NaHCO_3$ 4.8 mM, glucose 5.0 mM) foregassed with oxygen.
Acetylcholine chloride.

Procedure

A guinea pig is killed by a blow on its head and exsanguinated. The caudal part (about 15 cm) of ileum is removed and cleaned in Tyrode solution. Three ileum pieces (2.5–3.0 cm long) are cut and placed separately in 10 ml organ baths containing Tyrode solution. Each specimen is fixed to a pin in the bottom of the organ bath and connected through a spring to a Grass FT 03 transducer (isotonic measurement). The specimens are kept under a tone of 1.0 g. The concentrations are displayed on a Watanabe WTR 331 Linearcorder Mark III.

Concentration response curves to acetylcholine and test drugs are obtained by adding alternately acetylcholine and the test drugs in Tyrode solution to the both in 3–6 different concentrations. Each concentration is allowed to exert its maximal contracting effect before the tissue is washed and the next concentration is added.

From the concentration effect curves the IC50 values for acetylcholine and the test drugs are calculated by log-probit analysis.

$^3$—H-PrBCM binding to muscarinic cholinergic receptors

Whole brain minus cerebellum of a rat was homogenized in 10 vol icecold 0.32M sucrose, pH 7.4. The homogenate was centrifuged at 600 g for 10 minutes and the supernatant at 25000 g for 55 min. at 4° C. with rehomogenization of the pellet in 0.32M sucrose. Incubation tubes in triplicate received at 30° C. test substance and tissue suspension. After 10 min. of incubation ligand (NEN,28–44 Ci/mmol) was added (final conc. of $^3$H-PrBCM: 1.5 nM). After 15 min. of incubation the reaction was stopped by addition of sodiumthiosulphate. The samples were filtered through Whatman GF/B filters (25 mm). The tubes and filters were rinsed twice with buffer. Non-specific binding was determined in the presence of 2.5 μM atropine. IC50 values were calculated by log probit analysis.

| | Musc.agonism ileum ED50 n M | ³H—PrBCM binding brain IC50 n M | Isoniazide antagonism ED50 μmol/kg | Grid shock MED μmol/kg | Hot Plate ED50 μmol/kg |
|---|---|---|---|---|---|
| THPO | >13000 | >50000 | >1500 | >1500 | >90 |
| O—Methyl-THPO | 1800 | 45000 | 2.8 | 26 | 62 |
| O—Ethyl-THPO | 3400 | 6000 | 7.3 | >98 | >98 |
| O—Propyl-THPO | >13000 | 10000 | 50 | >91 | >91 |
| O—Isopropyl-THPO | >13000 | 3500 | 19 | >46 | >91 |
| O—Benzyl-THPO | >13000 | 32000 | 19 | >150 | >75 |
| O,5-Dimethyl-THPO | 830 | 27000 | 29 | 49 | 99 |
| O—Ethyl-5-Methyl-THPO | 1600 | 2400 | 41 | >91 | >91 |
| O—Methyl-5-Ethyl-THPO | >13000 | 15000 | 84 | 84 | N.D. |
| O—Methyl-5-Benzyl-THPO | >13000 | >50000 | 71 | >71 | >71 |
| O—Butyl-THPO | >13000 | 15000 | >170 | >170 | >86 |
| O—Isobutyl-THPO | >13000 | >13000 | 48 | >86 | >86 |
| O—Allyl-THPO | >13000 | 9600 | 23 | 46 | >92 |
| O—Crotyl-THPO | >13000 | 14000 | <43 | 170 | >87 |
| O—Propargyl-THPO | 1200 | 5800 | 3.0 | 11 | 86 |
| O,7-Dimethyl-THPO | 13000 | 12000 | 110 | 98 | >98 |

N.D. = not determined

The compounds of Formula I and the non-toxic acid addition salts thereof may be administered to animals such as dogs, cats, horses, sheeps or the like, including human beings, both orally and parenterally, and may be used for example in the form of tablets, capsules, powders, syrups or in the form of the usual sterile solutions for injection.—Results upon administration to human beings have been very gratifying.

Most conveniently the compounds of Formula I are administered orally in unit dosage form such as tablets or capsules, each dosage unit containing the free amine or a non-toxic acid addition salt of one of the said compounds in a amount of from about 0.10 to about 100 mg, most preferably, however, from about 5 to 50 mg, calculated as the free amine, the total daily dosage usually ranging from about 1.0 to about 500 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

Typical examples of formulas for composition containing 3-methoxy-4,5,6,7-tetrahydroisoxazolo[4,5-c]pyridinium chloride (called O-methyl THPO, HCl for short) as the active ingredient, are as follows:

(1) Tablets containing 5 milligrams of O-methyl THPO, HCl calculated as the free base:

| O—methyl THPO | 5 mg |
|---|---|
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |

(2) Tablets containing 50 milligrams of O-methyl THPO, HCl calculated as the free base:

| O—methyl THPO | 50 mg |
|---|---|
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |

(3) Syrup containing per milliliter:

| O—methyl THPO | 10 mg |
|---|---|
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

(4) Solution for injection containing per milliliter:

| O—methyl THPO | 50 mg |
|---|---|
| Acetic acid | 17.9 mg |
| Sterile water | ad 1 ml |

(5) Solution for injection containing per milliliter:

| O—methyl THPO | 10 mg |
|---|---|
| Sorbitol | 42.9 mg |
| Acetic acid | 0.63 mg |
| Sodium hydroxide | 22 mg |
| Sterile water | ad 1 ml |

Any other pharmaceutical tableting adjuvants may be used provided that they are compatible with the active ingredient, and additional compositions and dosage forms may be similar to those presently used for neuroleptics, analgesics or antidepressants.

Also combinations of the compounds of Formula I as well as their non-toxic acid salts with other active ingredients, especially other neuroleptics, thymoleptics, tranquilizers, analgetics or the like, fall within the scope of the present invention.

As previously stated, when isolating the compounds of Formula I in the form of an acid addition salt the acid is preferably selected so as to contain an anion which is non-toxic and pharmaceutically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, pamoates and maleates of the amines of Formula I. Other acids are likewise suitable and may be employed if desired. For example: fumaric, benzoic, ascorbic, succinic, salicylic, bismethylenesalicylic, propionic, gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals, animals, involving the neurotransmitters acetylcholine and muscarine, by administering to a living animal body, including human beings, an adequate quantity of a compound of Formula I or a nontoxic acid addition salt thereof. An adequate quantity would be from about 0.001 mg to about 10 mg per kg of body weight in each unit dosage, and from about 0.003 milligrams to about 7 milligrams/kg of body weight per day.

It is to be understood that the invention is not limited to the exact details of operation or exact compound or compositions shown and described, as obvious modifications and equivalents will be apparent to one skilled in the art.

We claim:

1. A tetrahydroisoxazolo 4,5-c pyridine derivative selected from those having the following formula:

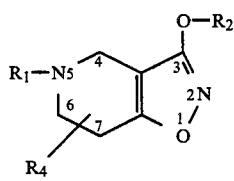

wherein $R_1$ is hydrogen, C1–C6 alkyl or phenyl-lower alkyl, in which the phenyl group may be substituted with halogen, lower-alkyl, or lower-alkoxy; $R_2$ is C1–C6 alkyl, C1–C6 alkenyl, C1–C6 alkynyl, or phenyl-lower alkyl, in which the phenyl group may be substituted with halogen, lower-alkyl, or lower-alkoxy, and $R_4$ is hydrogen or C1–C6 alkyl, or a pharmaceutically-acceptable acid addition salt thereof, provided that $R_2$ cannot be C1–C6 alkyl when both $R_1$ and $R_4$ are hydrogen.

2. A compound according to claim 1, in which $R_1$ is hydrogen or methyl, $R_2$ is methyl, ethyl, alkyl, 2-butenyl or 2-propynyl and $R_4$ is hydrogen or methyl.

3. A compound according to claim 1 or 2, in which $R_1$ is hydrogen or methyl, $R_2$ is ethyl, allyl, 2-butenyl or 2-propynyl and $R_4$ is hydrogen or methyl.

4. 3-Methoxy-5-methyl-4,5,6,7-tetrahydroisoxazolo 4,5-c pyridine, or a pharmaceutically acceptable acid addition salt thereof.

5. 3-Ethoxy-5-methyl-4,5,6,7-tetrahydroisoxazolo 4,5-c pyridine, or a pharmaceutically acceptable acid addition salt thereof.

6. 3-Methoxy-7-methyl-4,5,6,7-tetrahydroisoxazolo 4,5-c pyridine, an enantiomers thereof, or a pharmaceutically acceptable acid addition salt of either.

7. 3-Allyloxy-4,5,6,7-tetrahydroisoxazolo 4,5-c pyridine, or a pharmaceutically acceptable acid addition salt thereof.

8. 3-(2-Butenyloxy)-4,5,6,7-tetrahydroisoxazolo 4,5-c pyridine, or a geometric isomer thereof, or a pharmaceutically acceptable acid addition salt of either.

9. 3-(2-Propynyloxy)-4,5,6,7-tetrahydroisoxazolo 4,5-c pyridine, or a pharmaceutically acceptable acid addition salt thereof.

10. A pharmaceutical composition, useful for the treatment of a disorder caused by malfunction of the acetylcholine or muscarinic system, comprising a therapeutically-acceptable amount of a compound of the following formula:

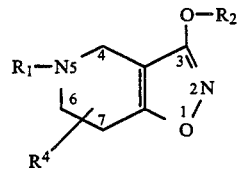

wherein $R_1$, $R_2$, and $R_4$ are are as follows: R1 is hydrogen, C1–C6 alkyl or phenyl-lower alkyl, in which the phenyl group may be substituted with halogen, lower-alkyl, or lower-alkoxy; R2 is C1–C6 alkyl, C1–C6 alkenyl, C1–C6 alkynyl, or phenyl-lower alkyl, in which the phenyl group may be substituted with halogen, lower-alkyl, or lower-alkoxy, and R4 is hydrogen or C1–C6 alkyl, or a pharmaceutically-acceptable acid addition salt thereof, together with a pharmaceutical carrier or excipient.

11. A pharmaceutical composition according to claim 10 wherein the active ingredient is present in an amount of from 0.1–100 milligrams per unit dose.

12. A pharmaceutical composition according to claim 10 or 11 wherein the active ingredient is a compound of claim 2.

13. A pharmaceutical composition according to claim 10 or 11 wherein the active ingredient is 3-methoxy-4,5,6,7-tetrahydroisoxazolo 4,5-c pyridine, or a pharmaceutically acceptable acid addition salt thereof.

14. Method for the treatment of a disorder, caused by malfunction of the acetycholine or muscarinic system, comprising the step of administering to a subject in need thereof a compound of the formula

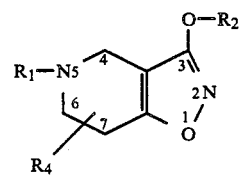

wherein $R_1$ is hydrogen, C1–C6 alkyl or phenyl-lower alkyl, in which the phenyl group may be substituted with halogen, lower-alkyl, or lower-alkoxy; $R_2$ is C1–C6 alkyl, C1–C6 alkenyl, C1–C6 alkynyl, or phenyl-lower alkyl, in which the phenyl group may be substituted with halogen, lower-alkyl, or lower-alkoxy, and $R_4$ is hydrogen or C1–C6 alkyl, or a pharmaceutically-acceptable acid addition salt thereof, in an amount effective for alleviation of said disorder.

15. Method of claim 14 wherein the compound administered is selected from the group consisting of 3-Methoxy-4,5,6,7-tetrahydroisoxazolo 4,5-c pyridine, 3-Ethoxy-4,5,6,7-tetrahydroisoxazolo 4,5-c pyridine, 3-Methoxy-5-methyl-4,5,6,7-tetrahydroisoxazolo 4,5-c pyridine, 3-Ethoxy-5-methyl-4,5,6,7-tetrahydroisoxazolo 4,5-c pyridine, 3-Methoxy-7-methyl-4,5,6,7-tetrahydroisoxazolo 4,5-c pyridine, 3-Allyloxy-4,5,6,7-tetrahydroisoxazolo 4,5-c pyridine, 3-(2-Butenyloxy)-4,5,6,7-tetrahydroisoxazolo 4,5-c pyridine, and 3-(2-Propynyloxy)-4,5,6,7-tetrahydroisoxazolo 4,5-c pyridine, enantiomers thereof, geometric isomers thereof, and pharmaceutically-acceptable acid addition salts of any of the foregoing.

16. Method of claim 14 wherein an amount of about 0.001–10 mg/kg of body weight of the compound is administered per unit dose.

* * * * *

UNITED STATES PATENT AND TRADEMARK OFFICE
CERTIFICATE OF CORRECTION

PATENT NO. : 4,608,378
DATED : August 26, 1986
INVENTOR(S) : Erik Falch, Povl Krogsgaard-Larsen, Per Sauerberg, Anne V. Christensen and Jens-Jorgen Larsen It is certified that error appears in the above-identified patent and that said Letters Patent is hereby corrected as shown below:

ol. 2, line 51; "herin" should read -- herein --
ol. 7, line 18; "phosphorous" should read -- phosphorus --
ol. 8, lines 8 and 18; "litterature" should read -- literature -- (both occurrences)
ol. 12, line 13; "heate" should read -- heated --
ol. 13, line 17; "ahd" should read -- and --
ol. 14, line 57; "3.75  H" should read -- 3.75 $^1$H --
ol. 19, line 53; "milliampermeter" should read -- milliamperemeter --
ol. 22, line 68; "pharmaceutically" should read -- pharmacologically --
ol. 23, line 26; delete "animals," (second occurrence)
ol. 23, line 64; "alkyl," should read -- allyl, --
ol. 24, line 8; "enantiomers" should read -- enantiomer -- ol. 24, line 34; delete "are" (second occurrence)

Signed and Sealed this

Tenth Day of March, 1987

*Attest:*

DONALD J. QUIGG

*Attesting Officer*   *Commissioner of Patents and Trademarks*